United States Patent [19]

Hahn

[11] Patent Number: 4,641,335
[45] Date of Patent: Feb. 3, 1987

[54] PRIMARY-BEAM COLLIMATOR FOR STEREO RADIOGRAPHIC X-RAY DIAGNOSTIC APPARATUS

[75] Inventor: Alfred Hahn, Erlangen, Fed. Rep. of Germany

[73] Assignee: Siemens Aktiengesellschaft, Berlin and Munich, Fed. Rep. of Germany

[21] Appl. No.: 720,321

[22] Filed: Apr. 5, 1985

[30] Foreign Application Priority Data

Jun. 15, 1984 [DE] Fed. Rep. of Germany ....... 3422343

[51] Int. Cl.$^4$ .............................................. G21K 1/04
[52] U.S. Cl. ...................................... 378/153; 378/41; 378/147; 378/150; 378/152
[58] Field of Search ................ 378/147, 150, 152, 153, 378/41, 42, 124

[56] References Cited

U.S. PATENT DOCUMENTS

| Re. 25,118 | 1/1962 | Graves | 378/150 |
|---|---|---|---|
| 2,214,621 | 9/1940 | Leishman | 378/42 |
| 3,683,186 | 8/1972 | Tompkins | 378/150 |
| 4,246,488 | 1/1981 | Hura | 378/153 |
| 4,566,112 | 1/1986 | Linde et al. | 378/2 |

FOREIGN PATENT DOCUMENTS 0000699 1/1984 Japan ...................................... 378/41

Primary Examiner—Craig E. Church
Assistant Examiner—John C. Freeman
Attorney, Agent, or Firm—Mark H. Jay

[57] ABSTRACT

A primary-beam collimator for a stereo radiographic x-ray diagnostic installation has an x-ray tube with dual focal points (F1, F2) arranged at a distance from each other. Shutter leaves (1a, 1b, 2a, 2b, 3a, 3b, 4a, 4b) are provided, and adjustable so that two beam pyramids (I from focal point F1, and II from focal point F2) can be individually controlled. Two internal shutter leaves (4a, 4b) are provided for restricting the beam in planes perpendicular to the stereo base F1–F2. These are adjustable between two external shutter leaves—each in the direction of its corresponding external shutter leaf. The internal shutter leaves (4a, 4b) are constructed so that, when adjusted to their external positions, they permit the emission of a central beam-pyramid from a central focal point (FN) and, together with the external shutter leaves (2a, 2b), they close the external shutter openings.

1 Claim, 3 Drawing Figures

PRIMARY-BEAM COLLIMATOR FOR STEREO RADIOGRAPHIC X-RAY DIAGNOSTIC APPARATUS

BACKGROUND OF THE INVENTION

The invention relates to a primary-beam collimator for a stereo radiographic x-ray diagnostic installation with an x-ray tube having dual focal points spaced at a distance from each other.

In such an arrangement the object under study is x-rayed alternately from each of the focal points. By simultaneously viewing the radiograph pair—obtained from two focal points—the observer perceives a spatial image. The use of such multifocal x-ray tubes presents the problem of ensuring adequate x-ray exposure of the relevant areas of the object examined, as sourced from each of the two focal points, while avoiding the exposure of more tissue than is required.

SUMMARY OF THE INVENTION

The principal object of the invention is to provide a primary-beam collimator of the type described above, by means of which each pyramid-shaped beam, originating from each focal point, can be optimally controlled.

This object, as well as other objects which will become apparent from the discussion that follows, are achieved, according to the invention, by providing shutters which can be adjusted so that each beam pyramid may be individually controlled for each focal point.

A further advantageous development of the invention consists in providing two external shutter leaves and two internal shutter leaves arranged between the external leaves so as to restrict the beams in planes perpendicular to the stereo base—i.e., the line connecting the two focal points—with each internal shutter leaf being adjustable in the direction of its corresponding adjacent external shutter leaf. The restriction of both beam pyramids in planes parallel to the stereo base can thus be achieved by means of a pair of shutter leaves common to both beam pyramids, while the restriction in planes perpendicular to the stereo base can be controlled by means of both external and internal shutter leaves for both beams. For this purpose the internal shutter leaves may be suitably shaped so that, when adjusted to their external positions, they permit the emission of a central beam pyramid from a central focal point and, in conjunction with the external shutter leaves, they close the external shutter openings. This configuration enables regular radiographs to be taken from a central focal point under the same optimal conditions of beam restriction as in the case of stereos.

For a full understanding of the present invention, reference should now be made to the following detailed description of the preferred embodiment of the invention and to the accompanying drawings.

DESCRIPTION OF THE PREFERRED EMBODIMENTS

Figure 1:
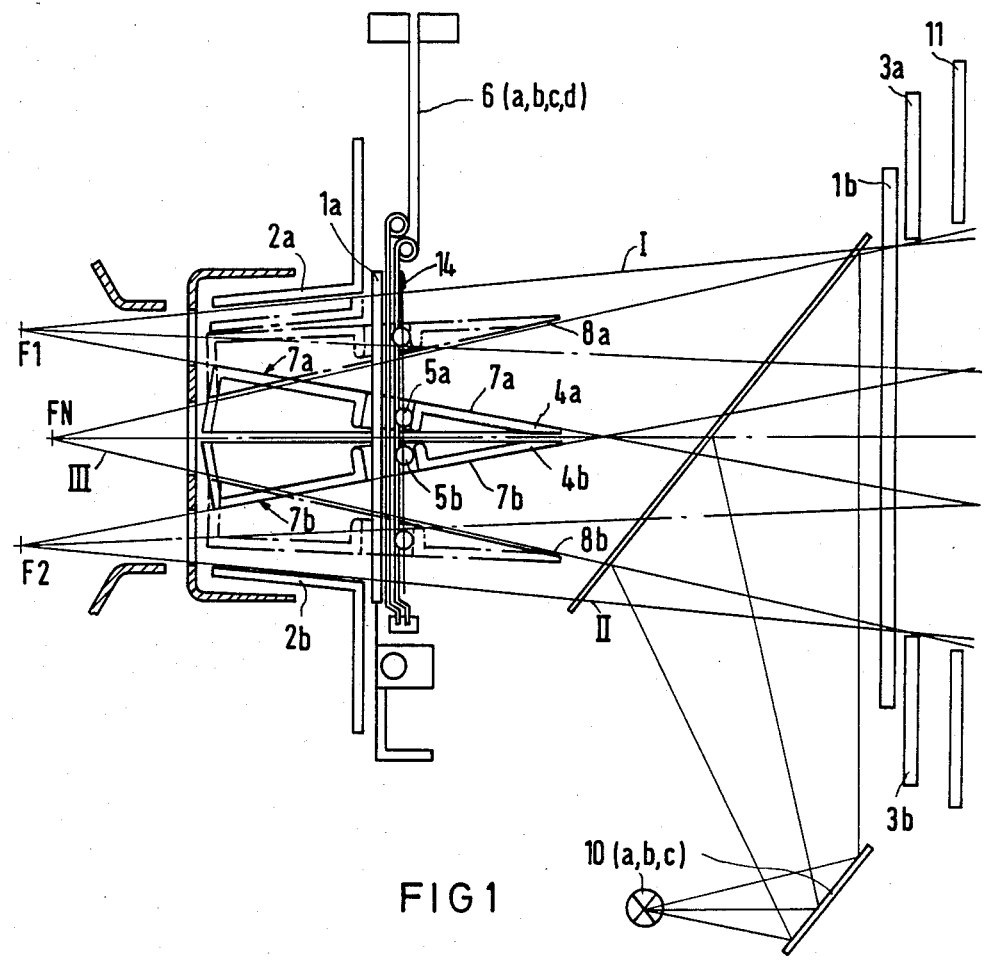
FIG. 1 is a cross-sectional view of a primary-beam collimator according to the invention.

FIG. 1 illustrates a primary-beam collimator which permits the restriction of three beam pyramids originating from three focal points: F1, F2 and FN. Focal points F1 and F2 serve to create pairs of stereo images, while focal point FN is used to produce regular radiographs. Beam restriction in planes parallel to the stero base (i.e., line F1–F2) is achieved as in the case of regular primary-base shutters, with the aid of first-stage and second-stage pairs of shutter leaves, 1a, 1b. Restriction in planes orthogonal to the stereo base is achieved during stereo operation (i.e., alternative activation of focal points F1, F2) with the aid of first-stage shutter leaves 2a (restricting the beam from F1), and 2b (restricting the beam from F2), and the second-stage shutter leaves 3a and 3b. Shutter leaves 2a, 2b, and 3a, 3b can be adjusted in a plane perpendicular to the central-beam axis of the restricted pyramid-shaped beam, in which the stereo base is located. Inner positions of leaves 2a, 2b have been represented by dash-dot lines.

Figure 3:
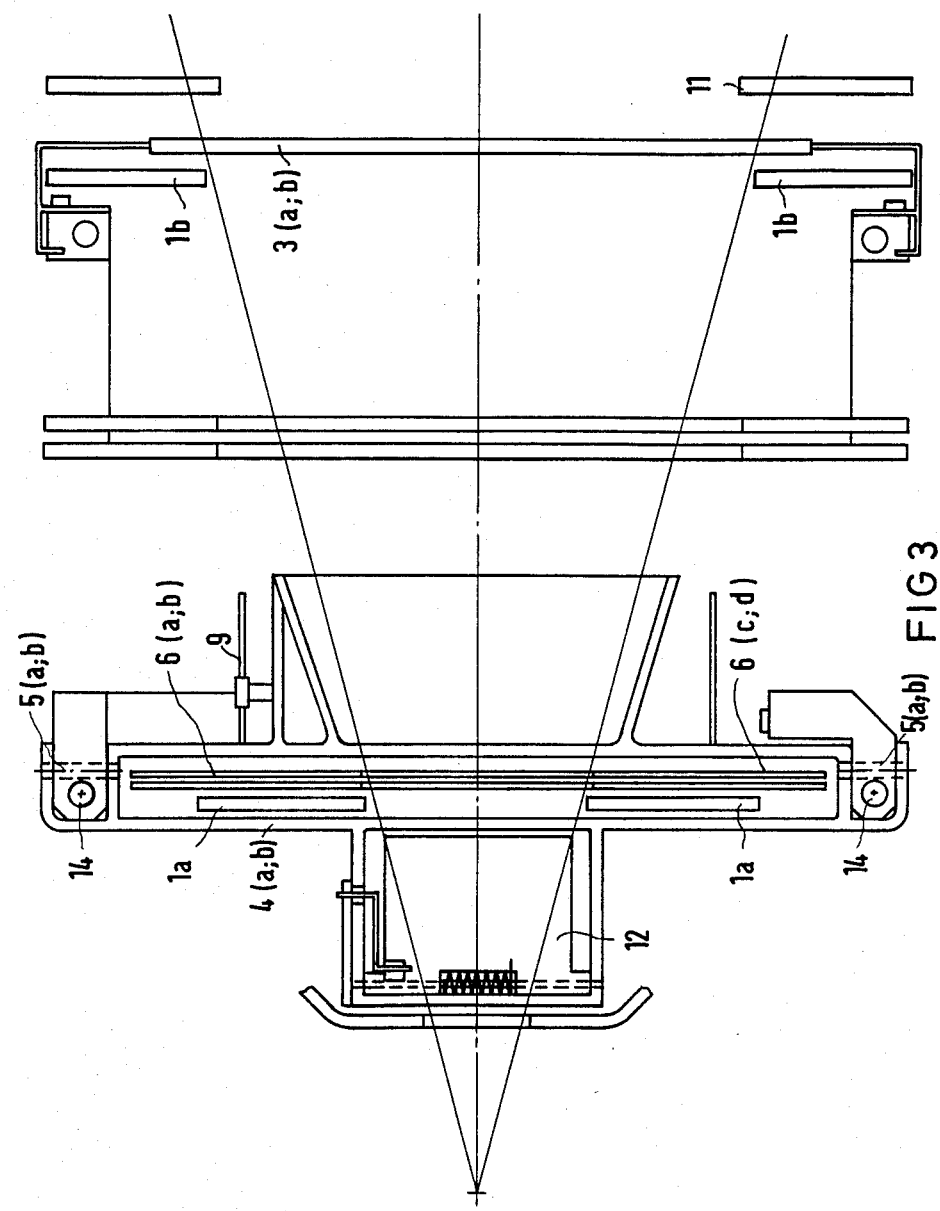
FIG. 3 is a cross-sectional view of the primary-beam collimator of FIG. 1, in a plane rotated 90° around the central beam axis.

Internal restriction of the beam pyramids is achieved by means of the swiveling shutter leaves 4a (for point F1) and 4b (for point F2). Shutter leaves 4a, 4b swivel about axes 5a, 5b, and can also be adjusted in a direction parallel to the stereo base on guides 14 (FIG. 3). Shutter leaves 2a, 2b, 3a, 3b, and the swiveling shutter leaves 4a, 4b, are operated by a stepping motor (not shown). Their movements are coordinated by a microcomputer.

In order to obtain pairs of stereo radiographs, shutter leaves 1a, 1b, 2a, 2b, 3a, 3b, and 4a, 4b are positioned as represented by solid lines, resulting in the shaping of two beam pyramids (I and II).

When shifting from stereo to regular operation, the microcomputer coordinates the movements of the shutter to new positions. Shutter leaves 2a, 3a, and swiveling shutter leaf 4a which, during stereo operation, restrict beam pyramid I at the top and the bottom, as shown in FIG. 1, now become the top restriction of beam pyramid III (with the vertex in FN). The same is valid for the bottom restriction, which is obtained with the aid of shutter leaves 2b, 3b, and 4b.

According to FIG. 3, the swiveling shutters 4a, 4b are constructed so as to allow free movement to shutter-leaf pairs 1a, 1b and filter frames 6a, 6b, 6c, 6d in a cross-section adjacent to axes 5a, 5b. During the stereo operation, restriction is achieved by external surfaces 7a, 7b (FIG. 2) of swiveling shutters 4a, 4b, while during regular operation restriction is performed by the internal surfaces 8a, 8b.

Figure 2:
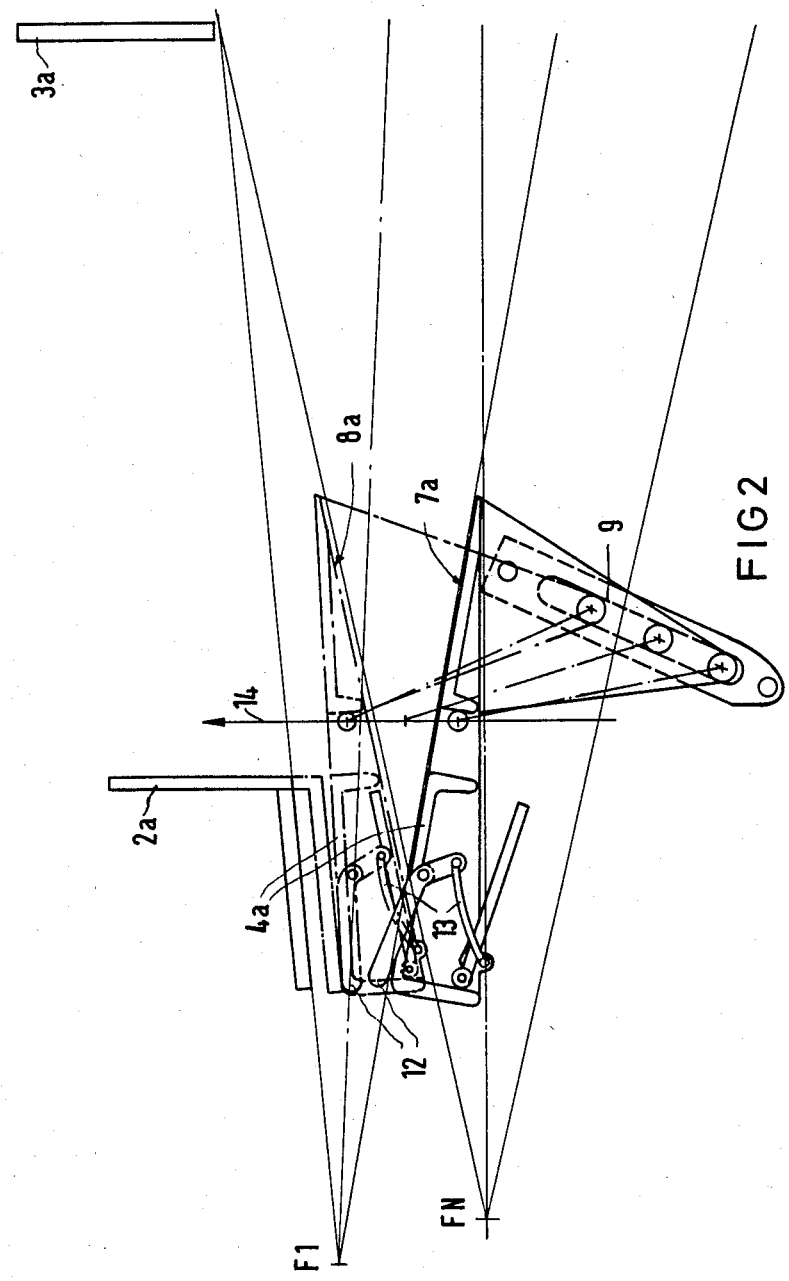
FIG. 2 is a detail of the primary-beam collimator shown in FIG. 1.

The swivel movement of swiveling shutters 4a, 4b takes place over a guide link 9 (FIG. 2).

In the space between the swiveling shutters 4a, 4b and shutter-leaf pair 1a, 1b a sighting device 10a, 10b, 10c may be provided, consisting of a light bulb and two mirrors (FIG. 1). For the operation of an image-intensifier tube with a circular entrance filter, it is possible to add an octagonal diaphragm 11, which is only schematically shown in the figures.

In the space between the swiveling shutters 4a, 4b an additional spring-operated swiveling shutter 12 may be introduced, as shown in FIGS. 2 and 3. During stereo operation with slight beam restriction, this swiveling shutter 12 closes the gap between the swiveling shutters 4a and 4b, cutting off scatter radiation. During regular operation, swiveling shutter 12 is kept open by shutter leaf 2a, now positioned along shutter leaf 4a, with the aid of a linkage rod 13.

An essential feature of the primary-beam collimator as shown in FIGS. 1 to 3 is the following: The shutter leaves 1a, 1b, 2a, 2b, 3a, 3b, and 4a, 4b are constructed and can be adjusted so that beam pyramids I and II, from focal points F1 and F2, respectively, can be individually controlled. For the restriction by planes perpendicular to the stereo base F1–F2, two internal shutter leaves 4a, 4b are provided, adjustable between two external shutter leaves 2a, 2b. The internal shutter leaves 4a, 4b are constructed so that, when brought to their external position, they permit the free emission of a central beam-pyramid III from a central focal point FN and, in conjunction with the external shutter leaves 2a, 2b, they close the external openings in the path of beam pyramids I, II.

The above-described primary-beam collimator can be used, as needed, for either regular or stereo shutter operation.

There has thus been shown and described a beam collimator for x-ray apparatus which fulfills all the objects and advantages sought therefor. Many changes, modifications, variations and other uses and applications of the subject invention will, however, become apparent to those skilled in the art after considering this specification and the accompanying drawing which discloses the preferred embodiment thereof. All such changes, modifications, variations and other uses and applications which do not depart from the spirit and scope of the invention are deemed to be covered by the invention which is limited only by the claims which follow.

What is claimed is:

1. An improvement to a stereo radiographic X-ray apparatus comprising first, second and third spaced-apart radiation focal points arranged such that the first and second focal points lie in a plane and the third focal point is located intermediate the first and second focal points in the plane, the improvement comprising:

first and second pairs of X-ray opaque shutter leaves, each pair of shutter leaves being associated with a corresponding one of the first and second focal points and positioned to collimate radiation therefrom in planes which are perpendicular to said plane and comprising an internal shutter leaf and an external shutter leaf which are so positioned that the two internal shutter leaves are adjacent each other between the two external shutter leaves and radiation from the third focal point can be collimated by the two internal shutter leaves; and means for independently moving the shutter leaves, such that each of the said pairs of shutter leaves can individually collimate radiation from its corresponding focal point for stereo radiography and the two internal shutter leaves can alternatively collimate radiation from the third focal point and to close shutter apertures through which radiation from the first and second focal points is directed.

* * * * *